United States Patent
Loesel et al.

(10) Patent No.: US 7,402,159 B2
(45) Date of Patent: Jul. 22, 2008

(54) SYSTEM AND METHOD FOR POSITIONING A PATIENT FOR LASER SURGERY

(75) Inventors: Frieder Loesel, Mannheim (DE); Klaus Baumeister, Sinsheim-Adersbach (DE); Ulrich von Pape, Landau i. d. Pfalz (DE); Thomas Sauter, Heidelberg (DE)

(73) Assignee: 20/10 Perfect Vision Optische Geraete GmbH, Heidelberg (DE)

( * ) Notice: Subject to any disclaimer, the term of this patent is extended or adjusted under 35 U.S.C. 154(b) by 836 days.

(21) Appl. No.: 10/790,625

(22) Filed: Mar. 1, 2004

(65) Prior Publication Data

US 2005/0192562 A1    Sep. 1, 2005

(51) Int. Cl.
*A61B 18/20*     (2006.01)
*A61B 3/16*      (2006.01)

(52) U.S. Cl. .............. 606/10; 606/5; 606/12; 351/208; 351/209

(58) Field of Classification Search ............ 606/4–6, 606/10–12, 166; 351/208, 209
See application file for complete search history.

(56) References Cited

U.S. PATENT DOCUMENTS

| | | | |
|---|---|---|---|
| 4,391,275 A | 7/1983 | Fankhauser et al. | |
| 4,443,075 A | 4/1984 | Crane | |
| 4,503,854 A | 3/1985 | Jako | |
| 4,517,980 A | 5/1985 | Tagnon | |
| 4,579,430 A | 4/1986 | Bille | |
| 4,702,575 A | 10/1987 | Breglia | |
| 4,718,418 A * | 1/1988 | L'Esperance, Jr. ............. 606/5 |
| 4,848,340 A | 7/1989 | Bille et al. | |
| 4,903,695 A | 2/1990 | Warner et al. | |
| 4,905,711 A | 3/1990 | Bennett et al. | |
| 4,994,058 A | 2/1991 | Raven et al. | |
| 5,108,412 A | 4/1992 | Krumeich et al. | |
| 5,226,903 A | 7/1993 | Mizuno | |
| 5,336,215 A | 8/1994 | Hsueh et al. | |
| 5,490,849 A * | 2/1996 | Smith ............................. 606/5 |
| 5,549,632 A * | 8/1996 | Lai ................................. 606/5 |
| 5,787,890 A | 8/1998 | Reiter et al. | |
| 5,807,380 A * | 9/1998 | Dishler .......................... 606/5 |
| 6,099,522 A * | 8/2000 | Knopp et al. .................. 606/10 |
| 6,254,595 B1 * | 7/2001 | Juhasz et al. ................... 606/5 |
| 6,373,571 B1 * | 4/2002 | Juhasz et al. ................. 356/399 |
| 6,406,473 B1 * | 6/2002 | Shimmick et al. .............. 606/5 |
| 6,562,026 B2 * | 5/2003 | Glockler ...................... 606/10 |
| 6,656,197 B1 * | 12/2003 | LaHaye ...................... 606/166 |
| 6,730,074 B2 * | 5/2004 | Bille et al. ..................... 606/5 |
| 6,964,659 B2 * | 11/2005 | Gross et al. .................... 606/5 |
| 7,018,376 B2 * | 3/2006 | Webb et al. .................... 606/4 |
| 2006/0020259 A1 * | 1/2006 | Baumeister et al. ............ 606/5 |
| 2006/0192921 A1 * | 8/2006 | Loesel et al. ................. 351/219 |

* cited by examiner

*Primary Examiner*—A. Farah
(74) *Attorney, Agent, or Firm*—Nydegger & Associates

(57) ABSTRACT

A system for positioning the eye of a patient, relative to a stationary surgical laser unit, includes a chair for moving the patient. An eye stabilizing element is held against the eye, with a tapered receptacle extending outwardly therefrom. Also, an alignment device with a tapered tip is mounted on the surgical laser unit. In operation, the patient is moved to engage the receptacle of the eye stabilizing element with the tip of the alignment device, to thereby align the patient's eye with the surgical laser unit for laser surgery.

15 Claims, 2 Drawing Sheets

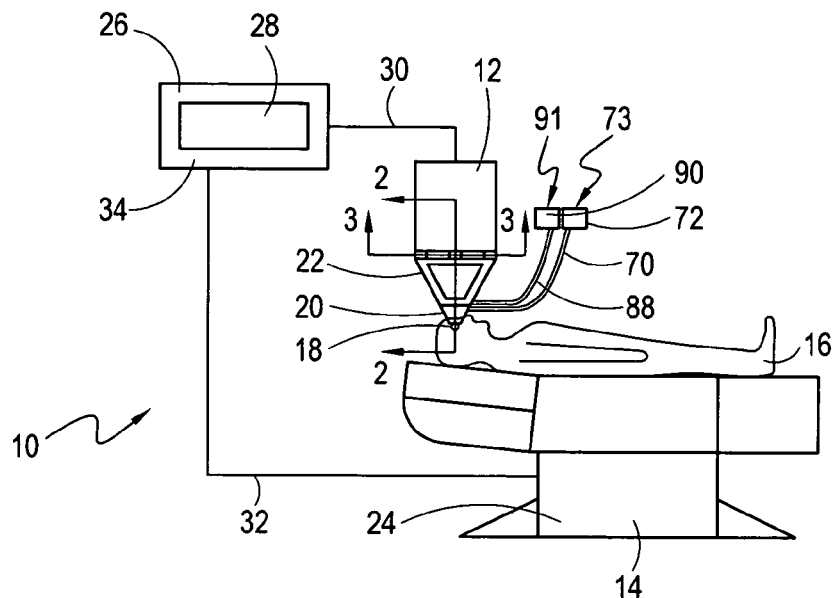
Fig. 1
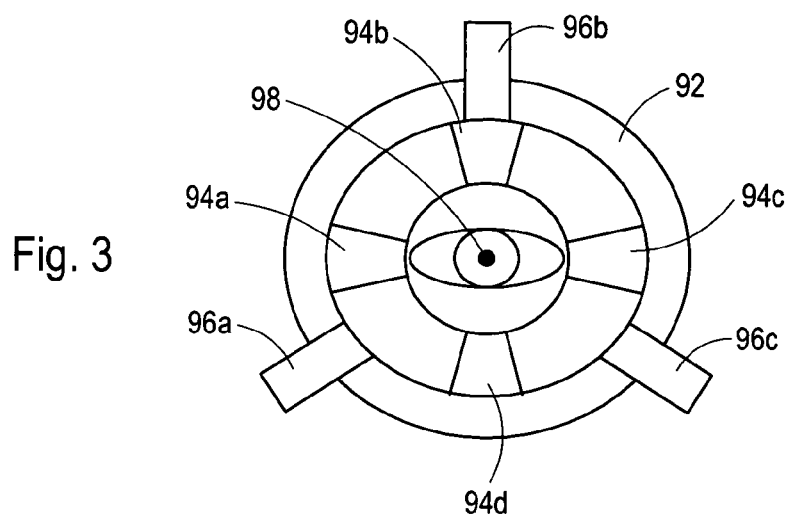
Fig. 3
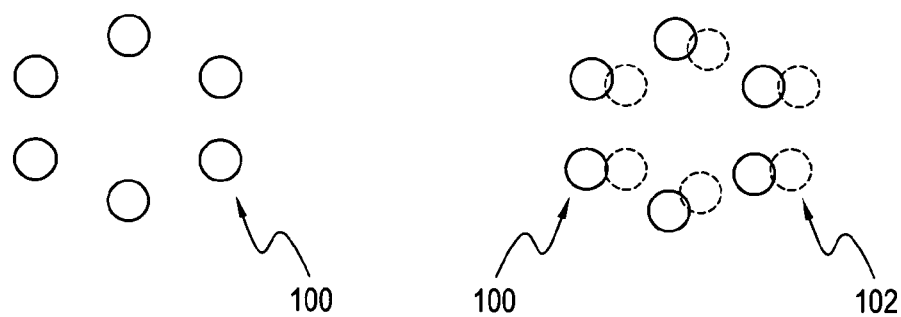
Fig. 4A
Fig. 4B

SYSTEM AND METHOD FOR POSITIONING A PATIENT FOR LASER SURGERY

FIELD OF THE INVENTION

The present invention pertains generally to systems for performing laser refractive surgery. More particularly, the present invention pertains to systems for positioning the eye of a patient for laser refractive surgery. The present invention is particularly, but not exclusively, useful as a system and method for moving the eye of the patient to a predetermined location relative to a stationary surgical laser unit for performing laser refractive surgery.

BACKGROUND OF THE INVENTION

The current state of the art in refractive laser surgery involves ablating corneal tissue of the eye with an ultra-fast, ultra-short pulse duration laser beam. Indeed, it is well known that the ablation of selected corneal tissue can correct refractive errors of a patient's eye by permanently altering the structure of the cornea. A system for accomplishing this type of tissue ablation through laser surgery is disclosed in U.S. Pat. No. 6,610,051, entitled "A Device and Method for Performing Refractive Surgery," which issued to Bille and is assigned to the same assignee as the present application, i.e. 20/10 Perfect Vision Optische Geraete GmbH.

Importantly, the nature of refractive laser surgery requires that the laser beam be precisely focused to a very small focal spot within the cornea. As such, the patient's eye must be stabilized, and the laser system must be properly and precisely aligned with the patient's eye. In order to achieve proper alignment between the eye of the patient and the laser system, the system alignment settings and operating parameters must be well defined, steadfastly maintained, and frequently verified. Further, as indicated above, it is well known to those skilled in the art that accurate and precise refractive surgery requires the corneal tissue be photoablated when the eye is substantially stabilized or stationary. As always, patient comfort and safety must be considered when holding the eye stationary and conducting the laser surgery.

In order to achieve the goal of maximizing results while minimizing risks to the patient during surgery, it is important to eliminate, or at least significantly reduce, as many system errors as possible. Included here is the improper alignment of the patient's eye, relative to the laser system. Interestingly, alignment errors may result from either a misconfiguration of the system, or from the patient's interaction with the system. Insofar as patient/system interaction is concerned, any voluntary or involuntary movement of the patient's eye during surgery can significantly alter the alignment of the eye relative to the laser system. It is necessary, therefore, to hold the eye of the patient stationary during any lasing procedure. Holding the eye stationary does not, however, necessarily require direct contact between the eye and the laser system. In fact, for several current laser surgery systems, the eye of the patient is not placed in physical contact with the laser system. When the eye is allowed to move independently of the system, however, maintaining an optical alignment of the eye with the laser system can be problematic. On the other hand, those systems wherein the eye of the patient is placed and held in direct contact with the laser system, maintaining optical alignment between the eye and the laser system, still poses problems.

For systems wherein a patient's eye is to be stabilized by placing the eye in direct contact with the system, stabilization can be established in either of two ways. For one, the patient can be pre-positioned as desired, and the system then moved into contact with the eye. Such systems, of course, must be capable of being reconfigured to establish the necessary optical alignment. For another, the laser system can be preconfigured with a desired optical alignment, and the patient then moved into contact with the system. Either way, there are alignment issues that need to be addressed. In the latter case, however, use of a preconfigured optical system avoids the difficulties that may arise due to extended displacements or altered orientations of the optical elements.

In addition to the operational issues discussed above, patient safety is always a concern. In particular, when the eye is in direct contact with the laser system, the magnitude of the interactive forces that are exerted on the eye are of concern. The several different events that can cause these forces to exceed the limits of safety need to be avoided.

In light of the above, it is an objective of the present invention to provide a system and method for positioning the eye of a patient relative to a laser system, for refractive laser surgery. Another object of the present invention is to provide a system and method for positioning the eye of a patient for refractive laser surgery, wherein alignment of the eye with the laser system is established by moving the patient, while the laser system remains stationary. Yet another object of the present invention is to provide a system and method for positioning the eye of a patient for refractive laser surgery which avoids damage to the eye while holding the eye substantially stationary during the laser surgery procedure. Still another object of the present invention is to provide a system and method for positioning the eye of a patient for refractive laser surgery that is easy to use, relatively simple to manufacture, and comparatively cost effective.

SUMMARY OF THE INVENTION

In accordance with the present invention, a system for positioning an eye of a patient for laser refractive surgery includes a surgical laser unit and a platform for supporting the patient during a surgical procedure. In addition to the platform and the laser surgical unit, the system of the present invention includes an eye stabilizing element which can be placed in direct contact with the anterior surface of the cornea of the patient's eye. Also, the system includes an alignment device for engagement with the eye stabilizing element. Notably, the alignment device may be mounted on the surgical laser unit, or, in the alternative, the alignment device may be integral to the surgical laser unit. In either case, this engagement between the eye stabilizing element and the alignment device, the eye is held in optical alignment with the laser unit during a surgical procedure.

Preferably, the platform is a chair having a motorized control assembly that can be selectively activated to move and reconfigure the chair. More specifically, the chair is moved to engage the eye stabilizing element on the patient's eye with the alignment device on the laser unit. For this purpose, the system includes a computer controller that is in electronic communication with both the motorized control assembly of the chair and the surgical laser unit. Further, the computer controller has a graphical user interface for presenting operational and system alignment information to a system operator.

Structurally, the eye stabilizing element for the present invention includes a hollow, substantially cylindrical shaped base member which defines a longitudinal axis, and which has a first end and a second end. A curved lens is centered on the axis, and is positioned at the first end of the base member to create an interior cavity between the lens and the base member. As intended for the present invention, the curved lens is shaped with a contact surface in the interior cavity that substantially conforms to the anterior surface of an eye.

The eye stabilizing element of the present invention also includes a hollow receptacle that is attached to the first end of the base member. More specifically, the receptacle is symmetrically oriented on the axis to surround the lens, and it includes a wall that extends away from the lens in a direction opposite to the base member. Importantly, this wall is formed with an interior surface that is preferably tapered with a decreasing diameter in an axial direction toward the lens.

Along with the structural aspects mentioned above, the eye stabilizing element of the present invention also includes a recessed vacuum channel that is formed at the periphery of the lens. Additionally, an air passage is formed in the wall of the receptacle for fluid communication with the vacuum channel. The receptacle of the eye stabilizing element also includes diametrically opposed tabs that extend radially from the wall of the receptacle for use in engaging the alignment device with the eye stabilization element.

Structurally, the alignment device of the present invention includes a hollow, tip member which has a wall that extends between an open first end and an open second end. Preferably, the wall is conical shaped, and the diameter of the tapered tip member decreases in the direction from the second end toward the first end. Importantly, the outer surface of the wall of the tip member is dimensioned to precisely engage with the interior surface of the wall of the receptacle of the eye stabilizing element. Further, the tip member includes a circumferential shelf that extends around the periphery of the first end of the tip member. This shelf may include a recessed vacuum groove that is formed in the shelf to extend around the periphery of the tip. Additionally, the alignment device of the present invention may also include a mounting ring for mounting the alignment device on the surgical laser unit.

Also included in the system of the present invention is a primary vacuum subsystem that is connected in fluid communication with the vacuum channel of the eye stabilizing element for creating a suction that holds the eye stabilizing element on the eye. More specifically, the primary vacuum subsystem includes a vacuum fitting that is attached to the vacuum channel, a vacuum line that is connected to the vacuum fitting, and a vacuum pump in fluid communication with the vacuum line. The system of the present invention may also include a secondary vacuum subsystem that is connected in fluid communication with the vacuum groove of the alignment device for creating a suction that holds the eye stabilizing element against the alignment device. As with the primary vacuum subsystem, the secondary vacuum subsystem similarly includes a vacuum fitting, a vacuum line, and a vacuum pump.

As contemplated by the present invention, the system further includes one or more pressure sensors that are mounted on the surgical laser unit. Specifically, the pressure sensors are positioned to contact the alignment device when the alignment device is positioned or mounted on the surgical laser unit. Preferably, when the alignment device is mounted on the laser unit, at least three sensors are positioned substantially equidistant from each other, and substantially equidistant from the center of the mounting ring. Further, a plurality of light sources are preferably mounted on the surgical laser unit for illuminating the eye during the laser surgery. It is to be appreciated, however, that a single light source may be used.

In the operation of the present invention, the alignment device is mounted, or positioned, on the laser unit. The patient is then seated in the chair, and the chair is moved and reconfigured for the surgical procedure. Initially, the motorized control assembly directs the movement of the chair to generally align the eye of the patient with the surgical laser unit. Once the eye has been generally aligned with the surgical laser unit, the eye stabilizing element is placed on the eye. More specifically, the interior cavity of the eye stabilizing element is placed over the eye to place the anterior surface of the cornea in contact with the contact lens. After the eye stabilizing element is placed on the eye, the primary vacuum subsystem is activated. As indicated above, the vacuum pump is used to create a suction between the contact lens of the eye stabilizing element and the anterior surface of the cornea, thereby holding the eye stabilizing element immovable against the eye.

With the eye stabilizing element held on the eye, and the alignment device positioned on the surgical laser unit, the chair is reconfigured to move the eye stabilizing element into an engagement with the alignment device. During this docking procedure, the eye stabilizing element is moved to precisely engage the interior surface of the receptacle of the eye stabilizing element with the outer surface of the hollow tip member of the alignment device. When properly engaged, the tabs of the eye stabilizing element will abut the shelf of the alignment device. In the preferred embodiment of the present invention, the secondary vacuum subsystem is then activated to create a suction force at the interface of the tabs and the shelf to maintain the engagement of the eye stabilizing element with the alignment device.

During a "docking" procedure as described above, the interactive forces that are generated between the eye stabilizing element and the alignment device are measured by the pressure sensors mounted on the surgical laser unit. These measured forces can then be used by the computer controller to calculate the magnitude and direction of the forces being exerted against the eye. If the forces calculated by the computer controller exceed acceptable limits, the procedure is stopped.

Throughout the course of the laser surgery, whenever a plurality of light sources are used to illuminate the eye, an observable pattern of reflected light is generated. Further, the observed pattern of reflected light may be compared to a pattern of light (i.e. a circle) that is indicative of a proper engagement between the eye stabilizing element and the alignment device. If the pattern of observed reflected light is substantially distorted from the desired pattern of light, the engagement is not correct and should be checked. After verifying a proper engagement of the eye stabilizing element with the alignment device, and ensuring the forces being exerted on the eye are within safety limits, the system operator may proceed with the refractive laser surgery.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a schematic view of a system, in accordance with the present invention, for positioning the eye of a patient for refractive laser surgery;

FIG. 3 is a top view of a plurality of pressure sensors in contact with an alignment device of the present invention, as seen along the line 3-3 in FIG. 1;

FIG. 4A is a representation of a pattern of reflected light indicating a proper engagement between an eye stabilizing element and an alignment device of the present invention; and FIG. 4B is a representation of a distorted pattern of reflected light indicating an improper engagement between an eye stabilizing element and an alignment device of the present invention.

DESCRIPTION OF THE PREFERRED EMBODIMENTS

Figure 2:
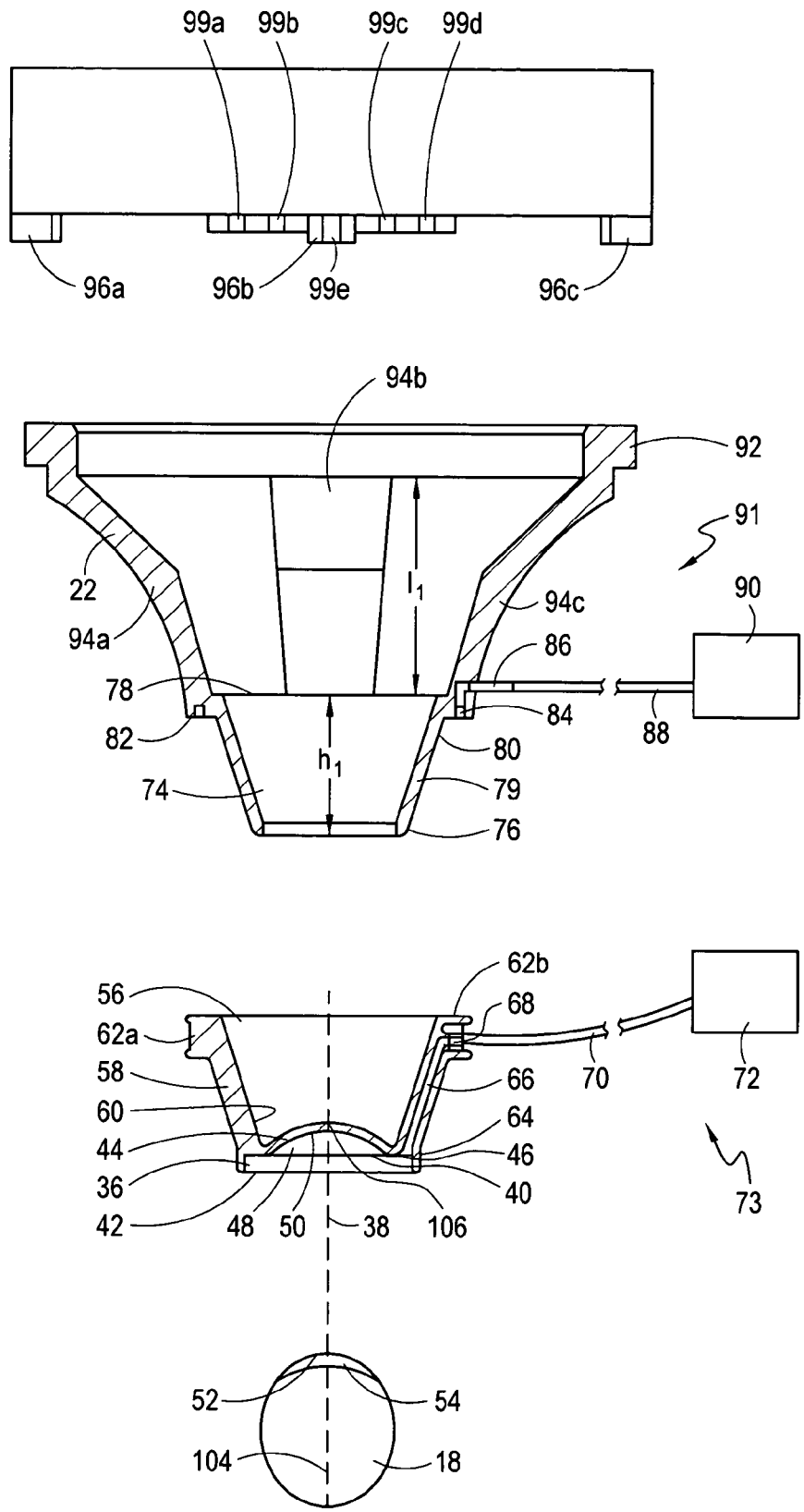
FIG. 2 is an exploded view, in partial cross section, of an eye stabilizing element, an alignment device, and a surgical laser unit of the present invention, as seen along the line 2-2 in FIG. 1.

A system in accordance with the present invention is shown in FIG. 1 and is generally designated 10. As shown, the system 10 includes a stationary surgical laser unit 12 and a platform 14. More specifically, as disclosed herein, the platform 14 is used for supporting a patient 16, and positioning an eye 18 of the patient 16 relative to the surgical laser unit 12 during a laser surgery. Further, system 10 includes an eye stabilizing element 20 which is placed on the eye 18 and an alignment device 22 that is mounted or positioned on the laser unit 12 for engagement with the eye stabilizing element 20. Specifically, the alignment device 22 may be mounted on the surgical laser unit 12, or the device 22 may be integral to the surgical laser unit 12.

In the preferred embodiment of the present invention the platform 14 is a chair that includes a motorized control assembly 24 which can be selectively activated to move and reconfigure the chair 14. As shown in FIG. 1, the system 10 also includes a computer controller 26 which has a graphical user interface 28 for receiving instructions from, and presenting information such as alignment and system functionality data to, a system operator (not shown). Further, the computer controller 26 is in electronic communication with the motorized control assembly 24 of the chair 14 for directing the movement of the chair 14, and with the surgical laser unit 12 for controlling the settings, timing and functioning of the unit 12. Specifically, an electrical cable 30 connects the computer controller 26 to the surgical laser unit 12. Additionally, an electrical cable 32 is connected from the computer controller 26 to the motorized control assembly 24. Also, the system 10 of the present invention includes a console 34 for housing the computer controller 26.

Referring now to FIG. 2, the eye stabilizing element 20 of the present invention is shown to include a hollow, substantially cylindrical shaped base member 36 which defines a longitudinal axis 38. More specifically, the base member 36 includes an open first end 40 and an open second end 42. The eye stabilizing element 20 also includes a curved lens 44 that is centered on the axis 38 with the periphery 46 of the lens 44 in contact with the first end 40 of the base member 36. Thus, the curved lens 44 is positioned to create an interior cavity 48 between the lens 44 and the base member 36. As intended for the present invention, the curved lens 44 is shaped with a concave contact surface 50 that will substantially conform to the anterior surface 52 of the cornea 54 of the eye 18. For this purpose, the contact surface 50 of lens 44 will have a radius of curvature that is greater than 5 mm. Preferably, the radius of curvature is approximately 8.8 mm. As contemplated by the present invention, the eye stabilizing element 20 can be made of any of a type of materials well known in the pertinent art. Notably, the lens 44 must be a clear, transparent material such as Poly(methyl methacrylate), also known as "PMMA".

Extending outwardly from the base member 36 is a hollow receptacle 56 that is attached to the first end 40 of the base member 36. As shown in FIG. 2, the receptacle 56 includes a wall 58 that is symmetrically oriented on the axis 38 to surround the lens 44 and extend axially away from the lens 44. Importantly, the wall 58 is formed with an interior surface 60 that is preferably tapered inwardly, which is to say the diameter of the taper decreases in an axial direction toward the lens 48. In addition, the receptacle 56 of the eye stabilizing element 20 also includes diametrically opposed tabs 62a and 62b that extend radially from the wall 58 of the receptacle 56 for use in engaging the alignment device 22 with the eye stabilizing element 20.

As also shown in FIG. 2, the eye stabilizing element 20 includes a recessed vacuum channel 64 that is formed at the periphery 46 of the lens 44. Additionally, an air passage 66 is formed in the wall 58 of the receptacle 56 for fluid communication between the vacuum channel 64 and the tab 62b. A primary vacuum fitting 68 is in fluid communication with the air passage 66 at the point of termination in the tab 62b. As shown in FIGS. 1 and 2, the system 10 also includes a vacuum line 70 that is connected to the vacuum fitting 68. Additionally, a vacuum pump 72 is in fluid communication with the vacuum line 70 for evacuating the air passage 68 and the vacuum channel 60. Collectively, the vacuum fitting 68, line 70 and pump 72 constitute a primary vacuum subsystem 73.

Considering now the alignment device 22 of the present invention, it can be seen in FIG. 2 that the alignment device 22 includes a hollow tip member 74 having a first end 76 and a second end 78. In addition, both the first end 76 and the second end 78 of the tip member 74 are open. As shown, a wall 79 of the tip member 74 extends from the first end 76 toward the second end 78. Preferably, the wall 79 is a conical shaped wall 70 that is tapered with an increasing diameter from the first end 76 toward the second end 78. Importantly for the present invention, the outer surface 80 of the tip member 74 is dimensioned to precisely mate with the interior surface 60 of the wall 58 of the eye stabilizing element 20. FIG. 2 also indicates that the tip member 74 includes a shelf 82 which extends around the periphery of the second end 78 of the tip member 74. As can be appreciated by referring to FIG. 2, the shelf 82 may be formed with a circumferential vacuum groove 84 that extends around the periphery of the second end 78 of the tip member 74 and it is dimensioned to abut with the tabs 62a and 62b of the eye stabilizing element 20. A secondary vacuum fitting 86 is provided for establishing fluid communication with the vacuum groove 84. More specifically, as shown in FIGS. 1 and 2, the system 10 may include a vacuum line 88 and a vacuum pump 90 for evacuating air from the vacuum groove 84 through the vacuum fitting 86. Collectively, the vacuum fitting 86, line 88 and pump 90 constitute a secondary vacuum subsystem 91.

Still referring to FIG. 2, the alignment device 22 may include a mounting ring 92 for connecting the alignment device 22 to the surgical laser unit 12. Further, connected to the mounting ring 92 are a plurality of extension arms, of which 94a, 94b, 94c and 94d (FIG. 3) are exemplary. As shown, the extension arms 94a-d connect the mounting ring 92 to the second end 78 of the tip member 74 to position the mounting ring 92 at a length "$l_1$" from the tip member 74.

When the alignment device 22 is positioned on the laser unit 12, the alignment device 22 will contact one or more pressure sensors of which pressure sensors 96a, 96b and 96c are exemplary. Preferably, when in contact with the mounting ring 92, the pressure sensors 96a-c lie in a plane that is substantially parallel to the plane of the mounting ring 92. As best seen in FIG. 3, they are each positioned an equal distance from the center point 98 of the mounting ring 92. Also shown in FIG. 3 is the position of the pressure sensors 96a-c relative to each other. Specifically, the three pressure sensors 96a-c are equidistant from each other, i.e. positioned 120° apart.

Referring once again to FIG. 2, it can be seen that the preferred embodiment of the present invention includes a plurality of light sources mounted on the surgical laser unit 12, of which light sources 99a, 99b, 99c, 99d, 99e (shown in shadow) and 99f (not shown) are exemplary. Importantly, the light sources 99a-f are positioned on the surgical laser unit 12 to illuminate the eye 18 during the surgical procedure.

In the operation of the present invention, the patient 16 is positioned in the chair 14 and the eye stabilizing element 20 is placed on the eye 18. More specifically, the contact surface 50 of the lens 44 of the eye stabilizing element 20 interfaces with the anterior surface 52 of the cornea 54 of the eye 18. Following commands from the system operator, the computer controller 26 then directs the motorized control assembly 24 to move and reconfigure the chair 14. Specifically, the chair 14 is moved to generally align the eye 18 of the patient 16 with the stationary surgical laser unit 12. If not already connected, the primary vacuum line 70 is then connected to the primary vacuum fitting 68 and to the primary vacuum pump 72. When activated, the primary vacuum subsystem 73 evacuates air from the vacuum channel 64 through the air passage 66. The evacuation of the vacuum channel 64 creates a suction force at the interface of the contact surface 50 and the anterior surface 52 of the cornea 54. Further, the force induced by the suction (a relative vacuum in the range of approximately 150-600 mbar) draws and holds the anterior surface 52 of the cornea 54 against the contact surface 50 of the lens 44. Consequently, the eye stabilizing element 20 is held immovable against the eye 18. If for any reason the eye stabilizing element 20 is not properly seated on the eye 18, the partial vacuum will not form. In this case, an error message is displayed for the system operator on the graphical user interface 28 of the computer controller 26. Of note, the error message may be either a visual or an audio message.

Along with the eye stabilizing element 20 being placed and held on the eye 18, the alignment device 22 is mounted, as necessary, on the surgical laser unit 12. Specifically, the mounting ring 92 is secured to the surgical laser unit 12. When so mounted, the mounting ring 92 of the alignment device 22 contacts, and exerts a pressure against, the pressure sensors 96a-c. Throughout the laser surgery procedure, data from the pressure sensors 96a-c is communicated to the computer controller 26 via the electrical cable 30.

Once the alignment device 22 is mounted on the surgical laser unit 12, the chair 14 is moved through a "docking" procedure whereby the eye stabilizing element 20 is moved to engage with the alignment device 22. During this docking procedure, the outer surface 80 of the hollow tip member 74 of the alignment device 22 is engaged by the interior surface 60 of the wall 58 of the eye stabilizing element 20. As intended by the present invention, the interior surface 60 of the wall 58 is dimensioned to precisely match the dimensions of the outer surface 80 of the tip member 74. Additionally, the tabs 62a and 62b of the eye stabilizing element 20 mate with the shelf 82 of the alignment device 22.

During the docking procedure, the interactive forces that are generated between the eye stabilizing element 20 and the alignment device 22 are monitored by the pressure sensors 96a-c. It can be appreciated by those skilled in the art that the force magnitudes experienced by the pressure sensors 96a-c, and the differentials between the force magnitudes, can be used to determine the magnitude and direction of the forces exerted against the eye 18 during the docking procedure. In this way, the operation of the system 10 is monitored to ensure patient 16 safety, and to minimize the risk of unwanted damage to the eye 18. Specifically, whenever a predetermined force threshold is reached, either in the direction or the magnitude of the forces exerted on the eye 18, further movement of the patient 16 toward the surgical laser unit 12 is prevented by the computer controller 26. Stated differently, when the threshold force values are reached, the chair 14 and the patient 16 can only be moved in a direction away from the surgical laser unit 12.

When the eye stabilizing element 20 of the present invention is properly engaged with the alignment device 22, the eye 18 is aligned with the surgical laser unit 12. In addition, the eye 18 will be positioned at a known distance from the surgical laser unit 12. More specifically, the extension arms 94a-d establish a fixed distance "$l_1$" between the mounting ring 92 and the second end 78 of the tip member 74. Further, the height "$h_1$" of the tip member 74 is known and fixed as well. Thus, when the eye stabilizing element 20 is engaged with the alignment device 22, the lens 44 and cornea 54 are a known distance from the surgical laser unit 12, more specifically, a known distance from the cutting lenses (not shown) of the surgical laser unit 12. Importantly, in one embodiment of the present invention, the eye stabilizing element 20, the alignment device 22 and the cutting lenses may be concertedly moved axially relative to the longitudinal axis 38 formed by the eye stabilizing element 20. However, it is to be appreciated that the distance between the lens 44 of the eye stabilizing element 20 and the cutting lenses of the surgical laser unit 12 remains fixed, regardless of the concerted movement of the eye stabilizing element 20, the alignment device 22 and the cutting lenses.

An important aspect of the present invention is to maintain this fixed spatial relationship between the eye 18 and the surgical laser unit 12 during the course of the laser surgery. Consequently, the contact between the alignment device 22 and the eye stabilizing element 20 must be maintained. Preferably, to maintain the necessary contact the secondary vacuum subsystem 91 is activated. Specifically, the secondary vacuum line 88 is connected to the secondary vacuum fitting 86 and the secondary vacuum pump 90. Thereafter, the secondary vacuum pump 90 is used to evacuate the vacuum groove 84. The evacuation of the vacuum groove 84 creates a suction whereby the eye stabilizing element 20 is drawn against the alignment device 22. Of note, the interactive force that maintains the engagement is a minimal force, which is to say it can be overcome by a moderate force in the opposite direction. As such, if the pressures exerted on the eye 18 by the docking procedure exceeds threshold values, or if the patient 16 moves away from the surgical laser unit 12 after engagement, the alignment device 22 and the eye stabilizing element 20 may be disengaged without injuring the patient 16.

As the eye stabilizing element 20 is placed in contact with the alignment device 22, a proper engagement between the eye stabilizing element 20 and the alignment device 22 must be verified. To this end, the plurality of light sources 99a-f that are mounted on the surgical laser unit 12 may be used to help verify a proper engagement. Specifically, it happens that in addition to illuminating the eye 18, the light sources 99a-f also create a circular pattern of reflected light that is observable by the system operator. Referring now to FIG. 4A, an exemplary pattern of reflected light 100 is shown. Importantly, when the pattern of reflected light 100 is circular, the eye stabilizing element 20 is properly engaged and aligned with the alignment device 22. If, however, the eye stabilizing element 20 is not properly or fully engaged with the alignment device 22, the pattern of reflected light 100 will be displaced or distorted from its preferred orientation. In this situation, as shown in FIG. 4B, the pattern of light 102 is indicative of an improper engagement. Further, the system operator can observe the misaligned pattern of reflected light on the graphical user interface 28, and terminate the surgical procedure until such time as a proper engagement between the eye stabilizing element 20 and the alignment device 22 can be achieved. Once proper engagement is achieved, the laser surgery procedure may continue.

During a laser surgery procedure, the surgical laser unit 12 generates a laser beam that travels along a beam path that is substantially coincident with the center point 98 of the mounting ring 92. The laser beam then passes on the beam path substantially along the longitudinal axis 38 of the base member 36, and the optical axis 104 of the eye 18. Specifically, when the laser beam exits the surgical laser unit 12, it thereafter travels through both the alignment device 22, and its hollow tip member 74. After transiting the tip member 74, the laser beam is incident on the contact lens 44 of the eye stabilizing element 20 at or near the apex 106 of the curved lens 44. The laser beam then travels through the clear, plastic contact lens 44, and enters the cornea 54 of the eye 18 to accomplish the laser surgery.

While the particular System and Method for Positioning an Eye of a Patient as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for positioning an eye of a patient for laser surgery which comprises:
   a surgical laser unit for generating a laser beam;
   an eye stabilizing element formed with a receptacle;
   a means for holding said eye stabilizing element in contact with the anterior surface of the cornea of the eye to project said receptacle outwardly therefrom;
   an alignment device, mounted on said surgical laser unit, wherein said alignment device is formed with a tip, and further wherein said tip is dimensioned for mating engagement with said receptacle of said eye stabilizing element;
   at least one pressure sensor, mounted on said surgical laser unit, for measuring interactive forces between said alignment device and said eye stabilizing element;
   a means for determining pressures exerted on the eye using said measured interactive forces; and
   a means for moving the patient and said eye stabilizing element into engagement with said alignment device, for positioning the eye of the patient at a predetermined location relative to said surgical laser unit for laser surgery.

2. A system as recited in claim 1 wherein the receptacle of said eye stabilizing element is tapered, and further wherein the tip of said alignment device is tapered and dimensioned for precisely engaging with the tapered receptacle of said eye stabilizing element.

3. A system as recited in claim 1 which further comprises a plurality of light sources for illuminating the eye, wherein said light sources create an observable pattern of reflected light, and further wherein said observable pattern of reflected light can be compared to a predetermined pattern of light for verifying the positioning of the eye.

4. A system as recited in claim 1 wherein said moving means is a chair having a motorized control assembly for reconfiguring and moving said chair.

5. A system as recited in claim 1 wherein said eye stabilizing element is formed with a primary vacuum fitting, and further wherein the holding means
   of the system comprises:
   a primary vacuum line connected to said primary vacuum fitting; and
   a primary vacuum pump in fluid communication with said primary vacuum line.

6. A system as recited in claim 5 which further comprises a means for maintaining the engagement between said alignment device and said eye stabilizing element.

7. A system as recited in claim 6 wherein the alignment device has a secondary vacuum fitting, and wherein said maintaining means comprises:
   a secondary vacuum line attached to said secondary vacuum fitting;
   a secondary vacuum pump in fluid communication with said secondary vacuum line; and,
   a means for controlling a suction force induced by said vacuum pump, for maintaining a proper engagement between said eye stabilizing element and said alignment device.

8. A system as recited in claim 1 wherein said alignment device further comprises a mounting ring having a center point, and further wherein a first pressure sensor, a second pressure sensor, and a third pressure sensor are mounted on said surgical laser unit equidistant from said center point of said mounting ring, and equidistant from each other.

9. A method for positioning an eye of a patient for laser surgery which comprises the steps of:
   holding an eye stabilizing element in contact with the anterior surface of the eye, said eye stabilizing element being formed with a receptacle, with said receptacle extending outwardly from the eye when said eye stabilizing element is held thereon;
   mounting an alignment device on a surgical laser unit, wherein said alignment device is formed with a tip, said tip being dimensioned for mating engagement with said receptacle of said eye stabilizing element;
   moving said eye stabilizing element into engagement with said alignment device to position the eye of the patient at a predetermined location relative to said surgical laser unit for laser surgery;
   monitoring at least one pressure sensor mounted on said surgical laser unit, wherein said pressure sensor measures the interactive forces between said alignment device and said eye stabilizing element; and
   determining pressures exerted on the eve using said measured interactive forces.

10. A method as recited in claim 9 which further comprises the steps of:
    illuminating the eye with a plurality of light sources;
    observing a pattern of reflected light; and,
    comparing said pattern of reflected light to a predetermined pattern of light for verifying the positioning of the eye.

11. A method as recited in claim 9 wherein said holding step includes activating a primary vacuum pump to evacuate a vacuum channel formed in said eye stabilizing element, wherein the evacuation of said vacuum channel creates a suction force between said eye stabilizing element and the eye.

12. A method as recited in claim 9 wherein said moving step includes activating a motorized control assembly mounted in a chair, to move and reconfigure said chair.

13. A method as recited in claim 9 wherein said alignment device further comprises a mounting ring having a center point, and further wherein a first pressure sensor, a second pressure sensor, and a third pressure sensor are mounted on said surgical laser unit equidistant from said center point of said mounting ring, and equidistant from each other.

14. A system for positioning an eye of a patient for laser surgery which comprises:

a surgical laser unit for generating a laser beam;

an eye stabilizing element formed with a receptacle;

a means for holding said eye stabilizing element in contact with the anterior surface of the cornea of the eye to project said receptacle outwardly therefrom;

an alignment device, mounted on said surgical laser unit, wherein said alignment device is formed with a tip, and further wherein said tip is dimensioned for mating engagement with said receptacle of said eye stabilizing element;

a means for moving the patient and said eye stabilizing element into engagement with said alignment device, for positioning the eye of the patient at a predetermined location relative to said surgical laser unit for laser surgery; and a plurality of light sources for illuminating the eye, wherein said light sources create an observable pattern of reflected light, and further wherein said observable pattern of reflected light can be compared to a predetermined pattern of light for verifying the positioning of the eye.

15. A system as recited in claim 14 which further comprises:

at least one pressure sensor, mounted on said surgical laser unit, for measuring interactive forces between said alignment device and said eye stabilizing element; and, a means for determining pressures exerted on the eye using said measured interactive forces.

* * * * *